United States Patent [19]

Zletz

[11] Patent Number: 4,729,979
[45] Date of Patent: Mar. 8, 1988

[54] COPPER ALUMINUM BORATE

[75] Inventor: Alex Zletz, Naperville, Ill.

[73] Assignee: Amoco Corporation, Chicago, Ill.

[21] Appl. No.: 709,790

[22] Filed: Mar. 11, 1985

[51] Int. Cl.$^4$ .................. B01J 21/02; B01J 23/70; C01C 15/12
[52] U.S. Cl. .................................. 502/202; 502/204; 502/206; 502/207; 502/346; 423/279
[58] Field of Search ............... 502/202, 204, 206, 207, 502/346; 423/279

[56] References Cited

U.S. PATENT DOCUMENTS

| 1,956,585 | 5/1934 | Oglesby et al. | 502/18 X |
| 3,856,702 | 12/1974 | McArthur | 502/204 |
| 3,856,705 | 12/1974 | McArthur | 502/202 |
| 3,971,735 | 7/1976 | Asano et al. | 502/202 |
| 3,985,682 | 10/1976 | Cull et al. | 502/346 |
| 3,990,995 | 11/1976 | McArthur | 502/207 |
| 4,024,171 | 5/1977 | McArthur | 502/207 X |
| 4,034,061 | 7/1977 | McArthur | 502/204 X |
| 4,040,980 | 8/1977 | Matsuda et al. | 502/346 |
| 4,048,114 | 9/1977 | Saunders | 502/346 |
| 4,105,588 | 8/1978 | Balducci et al. | 502/346 X |
| 4,354,960 | 10/1982 | Hammer et al. | 502/206 X |
| 4,386,017 | 5/1983 | Nakamura et al. | 502/174 X |
| 4,504,597 | 3/1985 | Klas et al. | 502/346 X |

FOREIGN PATENT DOCUMENTS 2449493  4/1975  Fed. Rep. of Germany ...... 502/202

Primary Examiner—Helen M. S. Sneed
Assistant Examiner—William G. Wright
Attorney, Agent, or Firm—William H. Magidson; Ralph C. Medhurst

[57] ABSTRACT

Copper aluminum borate which is reducible under Temperature Programmed Reduction at a temperature no more than 350° C. and/or has a surface area of at least 5 m$^2$/g and a pore volume of at least 0.04 cc per gram.

23 Claims, No Drawings

COPPER ALUMINUM BORATE

This invention relates to copper aluminum borate which is at least partially reducible with hydrogen under Temperature Programmed Reduction (TPR) conditions at a temperature no more than 350° C. More particularly, this invention relates to a catalyst having a surface area of at least 5 square meters per gram and a pore volume of at least 0.04 cc per gram copper aluminum borate.

McArthur in U.S. Pat. Nos. 3,856,702; 3,856,705 and 4,024,171 discusses the characteristics of a good support and the preparation of a new aluminum borate support. The patentee states that it has long been the practice in the art to impregnate or otherwise distribute active catalytic metals upon support materials having desired properties of porosity, surface area, thermal and mechanical stability, and suitably inert chemical properties. All of these characteristics of the support are interrelated and contribute in an often unpredictable manner to the ultimate activity of the final catalyst in its intended use.

McArthur then points out that alumina-boria catalyst composites are known in the art, and in particular were extensively investigated at one time in the catalytic cracking art. However, it was in general considered desirable to retain a substantial surface area, above about 150 m$^2$/g in the final catalyst composite, and for this reason it was the practice to calcine such catalysts at relatively low temperatures below about 1,200° F., which is below the temperature required for the formation of crystalline aluminum borates. At the other extreme, U.S. Pat. No. 3,172,866 discloses catalyst supports prepared by calcining alumina-boria mixtures containing less than 5 weight percent boria at temperatures of 1,600°–1,800° C. (2,912°–3,272° F.), under which conditions the boria apparently sublimed out of the composite, and a final alpha alumina support having a surface area below 0.5 m$^2$/g is produced.

McArthur then states that he has found that for purposes of producing a catalyst of maximum activity and stability for high temperature, vapor phase conversions such as exhaust gas conversions, a much superior support is produced by calcining certain alumina-boria composites within the temperature range of about 1,250°–2,600° F. Calcination within this range appears to produce a definite crystalline phase of 9Al$_2$O$_2$.2B$_2$O$_2$ and also in most cases a crystalline phase of 2Al$_2$O$_2$.B$_2$O$_2$. Although calcining such composites at temperatures below or above the specified range can produce supports of adequate stability for some purposes, it appears that within the range of about 1,250°–2,600° F., an optimum combination of crystallinity, porosity, surface area, and/or chemical properties is produced, such that a distinct maximum activity is achieved from active metals supported on such supports. Also, such catalysts exhibit excellent thermal and mechanical stability up to temperatures of about 2,500°–3,000° F., depending mainly upon the type of active metals present.

McArthur states that after calcination the aluminum borate support can be impregnated with solution(s) of desired catalytic salt or salts, preferably those that are thermally decomposable to give the corresponding metal oxides and/or sulfides. Following impregnation, the finished catalysts are dried and, if desired calcined at temperatures of e.g. 500° to 1,000° F. In the final catalyst the active metal or metals may appear in the free form, as oxides or sulfides or any other active form.

Examples 1 to 6 of McArthur impregnate the calcined support with an aqueous solution of copper nitrate and cobalt nitrate to provide about 4% copper as CuO and 12% cobalt as Co$_2$O$_3$ in the final catalyst. The catalysts were tested after drying. Examples 11 to 16 used catalyst loadings of 8% copper as CuO and 8% cobalt as Co$_2$O$_3$. Example 21 produces a catalyst by impregnating the calcined aluminum borate with nickel nitrate salt followed by a second calcination. None of these examples disclose nor suggest the production of finely divided copper on an aluminum borate or copper aluminum borate support or the production of copper aluminum borate.

Uhlig discloses the preparation of a green tetragonal solid copper aluminum borate having the structure Cu$_2$Al$_6$B$_4$O$_{17}$ in Diplomarbeit, Institute for Crystallography, Aacken (October 1976) "Phasen—und Mischkristall—Bildung im B$_2$O$_3$—armeren Teil des Systems Al$_2$O$_3$-CuO-B$_2$O$_3$" "Formation of Phases and Mixed Crystals in that Part of the Al$_2$O$_3$-CuO-B$_2$O$_3$ System With a Low B$_2$O$_3$ Content" which is hereby incorporated by reference, by grinding together solid boron oxide, copper oxide and alumina, sealing the ground metal oxides in a platinum tube and heating same at 1000° C. over the heating period of 48 hours. Attempts to produce this copper aluminum borate by the indicated route yields well-defined, dense crystalline particles which have an extremely low surface area and are accordingly not suitable for many catalysis processes due to the low porosity and surface area. There is no indication therein that Uhlig's copper aluminum borate can be converted into a catalyst comprising finely divided copper on a copper aluminum borate or aluminum borate support.

Asano U.S. Pat. No. 3,971,735 discloses a copper, zinc, aluminum and boron catalyst useful in low temperature methanol synthesis. The catalyst is preferably produced by forming a mixture of water soluble salts of copper, zinc and boron, precipitating same with an alkali carbonate and mixing with alumina. The catalyst is then fired at approximately 300°–450° C. There is no disclosure in this reference of a catalyst comprising finely divided copper on a copper aluminum borate or aluminum borate support. Various other references such as Nakamura, U.S. Pat. No. 4,386,017, Hammer, U.S. Pat. No. 4,354,960 and Ganzler, U.S. Pat. No. 3,981,908 are cumulative to the aforesaid McArthur and Asano patents.

The general object of this invention is to provide a new class of catalysts. Other objects appear hereinafter.

In the discussion that follows, reference is made to Temperature Programmed Reduction. This test was carried out by placing $1.5 \times 10^{-4}$ moles of copper aluminum borate in a 0.6 mm outside diameter vycor tube heated by an electric furnace. The tube was purged with helium or argon by heating to 300° C. After cooling to ambient temperature, the gas feed to the vycor tube was switched to either 5% CO in He or 5% H$_2$ in Ar and the temperature was ramped to about 850° C. at 8° C./min. The temperature was controlled and ramped by a Eurotherm Model 125 programmer equipped with a 919 temperature controller. The change in gas composition of the effluent was detected with a thermal conductivity cell equipped with output to a strip-chart recorder. The carbon dioxide formed was removed from the effluent by a bed of ascarite and the water formed was removed by magnesium perchlorate. Unless otherwise stated, pore volume, surface area and average pore radius was determined by BET nitrogen adsorption (desorption test).

I have now found that copper aluminum borate ($Cu_{2-x}Al_{6-y}B_4O_{17}M_mM'_nM''_y$ wherein M is a divalent metal, M' is a monovalent metal, m ranges from 0 to 0.8, n ranges from 0 to 1.6, X ranges from 0 to 0.8 and is equal to the sum of $m+n/2$, M'' is a trivalent metal and y ranges from 0 to 1.2) which is at least partially reducible with hydrogen under Temperature Programmed Reduction conditions at a temperature no more than 350° C., preferably having a surface area of at least 5 m² per gram and a pore volume of at least 0.04 cc per gram is a new catalyst and further that copper aluminum borate can be treated with a reducing agent to form a catalyst comprising finely divided metallic copper (zero valent copper) on a support comprising an aluminum borate. Part of the copper in the copper aluminum borate of this invention reacts with a reducing gas at relatively low temperature (about 175° to 350° C.) to form finely divided copper on the aluminum borate support, whereas the highly crystalline copper aluminum borate of Uhlig's having a surface area of 0.2 m²/g or less does not start to react with hydrogen until about 475° C. When Temperature Programmed Reduction was used to distinguish the Uhlig crystalline material having a surface area of 0.2 m²/g versus the higher surface area material of this invention, it was found that (1) copper aluminum borate of this invention having a surface area of 86 m²/g started to be reduced with hydrogen at 175° C., had a sharp peak, about 75% of the theoretical amount of hydrogen had reacted by 416° C. and about 86% of the theoretical amount of hydrogen gas consumed by the time the temperature reached 700° C., (2) copper aluminum borate having a surface area of 7 m²/g started to be reduced at 246° C., had a broad peak, and the theoretical amount of hydrogen was consumed at 842° C. and (3) the copper aluminum borate of Uhlig did not begin to react with hydrogen until about 475° C., did not have a peak and was still slowly reacting with hydrogen at 842° C. at which point 16% of the theoretical amount of hydrogen had been consumed and after standing at 842° C. for 27 minutes the experiment was stopped with a total hydrogen consumption of 27% of theory. Accordingly, the higher surface area copper aluminum borate of this invention reacts at a much lower temperature, at a faster rate and more completely than Uhlig's lower surface area copper aluminum borate.

When copper aluminum borate is used as a catalyst in the dehydrogenation of organic compounds or in a reaction medium containing a reducing gas, at least part of the copper in the copper aluminum borate is converted into finely divided copper on an aluminum borate support. In some reactions, such as in the dehydrogenation of alkylaromatics to alkenylaromatics, substantially all of the copper in the still active catalyst can be present as finely divided copper metal on an aluminum borate support, i.e., in the aluminum borate matrix. In other cases, the active catalyst always contains some copper aluminum borate. If part of the copper in copper aluminum borate is replaced with another divalent metal, copper in the compound is still reducible to metallic copper at relatively low temperature but no evidence has been found that other divalent metals are reduced at low temperatures. To the best of my knowledge, complete replacement of the copper with another divalent metal followed by treatment with a reducing gas requires substantially higher temperatures to form finely divided metallic particles on the support. Accordingly, copper aluminum borate is unique. Copper on an aluminum borate support is the subject of my copending application Ser. No. 710,015 filed on even date.

If neat copper aluminum borate having the empirical formula $Cu_2Al_6B_4O_{17}$ is viewed as having the structure $3Al_2O_3.2CuO.2B_2O_3$, the reduction with CO or $H_2$ can be represented in its simplest terms as follows:

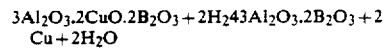

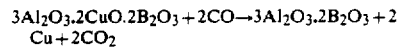

X-ray diffraction patterns of the products indicate that the aluminum borate crystal has the formula $2Al_2O_3.B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB and aluminum borate. The X-ray diffraction patterns in Table I show the significant lines for unreduced CuAB, substantially fully reduced CuAB (copper on aluminum borate) of this invention, CuAB of Uhlig, $Al_4B_2O_9$ and copper.

X-ray data were determined by standard techniques. The radiation was the K-alpha double of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in A, corresponding to the recorded lines, were calculated. In Table I the relative intensities are given in terms of the symbols VVS=very very strong (over 100), VS=very strong (80–100), S=strong (50–80), M=Medium (20–50), W=weak (10–20) and VW=very weak (<10).

TABLE I

| dA | Cu on AB | Cu AB | Uhlig Cu AB | $Al_4B_2O_9$ | Cu |
|---|---|---|---|---|---|
| 7.50 ± .1 | | VW–M | M | | |
| 5.29 ± .05 | VS | VS | VS | VS | |
| 5.00 ± .05 | | S | S | | |
| 4.92 ± .03 | W–M | | | W | |
| 3.73 ± .03 | | W–M | W | | |
| 3.64 ± .03 | | VW–W | VW | | |
| 3.58 ± .03 | VW–M | | | VW | |
| 3.35 ± .03 | VW–M | W | W | M | |
| 2.98 ± .03 | | VW–W | W | | |
| 2.84 ± .03 | | VW–W | VW | | |
| 2.78 ± .02 | VW | | | | |
| 2.64 ± .02 | M | M–S | M | M | |
| 2.61 ± .02 | | W–M | W | | |
| 2.50 ± .02 | | W–M | VW | | |
| 2.45 ± .02 | W–M | | | W | |
| 2.26 ± .02 | | W–M | W | | |
| 2.22 ± .02 | W | | | VW | |
| 2.16 ± .02 | | M | W | | |
| 2.13 ± .02 | M | | | W–M | |

TABLE I-continued

| dA | Cu on AB | Cu AB | Uhlig Cu AB | Al₄B₂O₉ | Cu |
|---|---|---|---|---|---|
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction lines of the Al₄B₂O₉ and copper.

The significant X-ray diffraction lines for copper aluminum borate are set forth below in Table A.

TABLE A

| dA | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

As indicated below, the catalyst of this invention can be used for oxidation, dehydrogenation, conversion of syn gas (This is the subject of application Ser. No. 710.042 filed in the name Zletz et al), hydrogenation (This is the subject of application Ser. No. 710,016 filed in the name of Kouba et al), etc.

For purposes of this invention the term "aluminum borate" is used in the generic sense to be inclusive of all aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate, comprising the X-ray diffraction pattern of $Cu_2Al_6B_4O_{17}$, such as pure or neat copper aluminum borate, copper zinc aluminum borate, aluminum borate/copper aluminum borate, copper aluminum borate/copper chromite, copper aluminum borate/alumina, etc.

Briefly, the copper aluminum borate of this invention can be prepared by a three-step procedure which comprises (1) combining a source of divalent copper, trivalent aluminum and boron in the form of the oxide or borate, (2) drying the composition where necessary to remove water or diluent and (3) calcining the composition at a temperature sufficiently high to form crystalline copper aluminum borate preferably having an X-ray diffraction pattern for $Cu_2Al_6B_4O_{17}$ set forth in Table A.

While the copper aluminum borate of this invention can be prepared by various techniques, it is generally preferred to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatilized during the subsequent drying and/or calcination step. The presence of volatile components in preparation of copper aluminum borate, such as water, $NH_3$, acetate ion, nitrate ion, etc. is advantageous in providing the copper aluminum borate with relatively high surface area and porosity desirable for most catalytic reactions.

Accordingly, sources of copper for use in this invention include copper nitrate, copper acetate, copper carbonate, copper borate, etc. since the nitrate, acetate and carbonate anions are destroyed during the drying or calcination step. Suitable sources of boron include boric acid, copper borate, aluminum borate, boron oxides and ammonium borate. The aluminum can be present in the form of alumina sols, aluminum nitrate, alumina, aluminum acetate, aluminum borate, etc. As shown in Example III, it is generally desirable to employ ammonium salts or ammonium hydroxide to increase the surface area and porosity of the copper aluminum borate. These components can be combined in an aqueous medium in approximately stoichiometric proportions to provide $Cu_2Al_6B_4O_{17}$. In some cases (methanation) it is desirable to have excess aluminum and borate present in the catalyst precursor in order to form a crystalline mixture of copper aluminum borate/aluminum borate.

If desired, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been substantially incorporated into copper aluminum borate crystals and accordingly X in the above formula can range from about 0.01 to 0.8, preferably about, 0. 05 to 0.50. Trivalent metal ions can appear as M" in the above formula, e.g., $Fe^{+++}$. However, chromium forms a chromite and appears not to replace aluminum.

While it is generally preferred to produce neat copper aluminum borate or copper aluminum borate/aluminum borate catalysts, the partial replacement of aluminum with chromium (about 5 to 30%) yields an excellent hydrogenation catalyst (copper aluminum borate/copper chromite) for conversion of alkyl succinates to butanediol and dehydrogenation catalyst for conversion of alkylaromatics to alkenylaromatics. Dehydrogenation of cumene to α-methylstyrene over an 80% Cu/20% zinc composition gave a nearly colorless product compared with a slightly yellow color from CuAB. The preparation with copper chromite can be used for dehydrogenating cumene, but showed dealkylation activity for p-cymene and p-ethyltoluene. The copper 90% Al-10% Fe borate gave lower conversion of cumene and p-ethyltoluene to the corresponding styrenes, but selectivities to dehydrogenated products were better than for CuAB. Likewise conversion of ethylbenzene to sytrene was lower than CuAB; catalytic activity did not deteriorate, whereas it does so rapidly with undoped CuAB. Dehydrogenation of alkylaromatics is the subject of copending application Ser. No. 710,043 in the name of Satek filed on even date, which is hereby incorporated by reference.

If desired, non-volatile cations such as alkali metal (M' in the above formula) or alkaline earth metal cations can be present during the preparation of the copper aluminum borate. For example, it has been found that if finely divided copper aluminum borate is prepared from a composition containing potassium ions and the catalyst is used in the conversion of syn gas to methanol only single carbon chain compounds are produced, (e.g., methanol and methyl ethers). If no alkali metal is present during the preparation of the copper aluminum borate but potassium is present as a result of doping the crystalline copper aluminum borate, a mixture of alcohols comprising methanol, ethanol, propanol, etc. is produced.

In somewhat greater detail, the copper salt and boron compound are desirably dissolved in water together with a water soluble aluminum salt and/or alumina in the form of sols or powder. The composition is dried (e.g. at atmospheric pressure or under vacuum) and then calcined to a temperature of about 650° C. to 1000° C., preferably at least 700° C. for syn gas catalysts and at least 800° C. for dehydrogenation catalysts for about 0.1 to 24 hours, typically in air. The higher the calcination temperature the shorter the calcination time. Calcination at about 680° C. for about 3 hours generally leads to about 20% crystallinity of copper aluminum borate while calcination at about 845° C. for about 3 hours generally leads to about 80% crystallinity. Calcinations below about 800° C. tend to provide a catalyst that is more active in syn gas conversion. Calcinations above about 800° C. tend to provide a blue green crystalline material that is more active in dehydrogenation reactions than the green crystalline material obtained below about 800° C. Other things being equal the higher the calcination temperature the lower the surface area and porosity of the copper aluminum borate. For example, copper aluminum borate calcined at 830° C. had a surface area of 19 m²/g, pore volume 0.1639 cc/g and 293Å average pore radius whereas the same material calcined at 925° C. had a surface area of 7 m²/g, pore volume 0.0402 cc/g and 334Å average pore radius. Of course, the optimum calcination temperature is dependent on the particular composition calcined, the calcination time, the volatiles present during the preparation of the composition and the desired surface area and porosity.

The calcined copper aluminum borate can be used for oxidation, dehydrogenation, conversion of syn gas, hydrogenation, etc. or treated with reducing gas, such as hydrogen or carbon monoxide at a temperature of from about 150° C. to 1000° C. to convert them into catalysts comprising finely divided metallic copper on a support comprising aluminum borate. The higher the temperature of the reducing gas and the more effective the reducing agent, the lower the concentration of copper aluminum borate and the higher the concentration of neat aluminum borate in the support. If the copper aluminum borate is used directly as a catalyst without pretreatment with a reducing gas, the copper aluminum borate is converted into a catalyst comprising finely divided copper on a support comprising aluminum borate by any reducing gas present in the reaction. For example, syn gas and hydrogenation reactions use reducing gases while dehydrogenation produces hydrogen.

Either prior to or after the conversion of the copper aluminum borate to the catalyst comprising finely divided copper on a substrate or support comprising aluminum borate, the aluminum borate can be treated with any of the metals or metal compounds conventionally used in catalysis. For example, as indicated above, the copper aluminum borate can be treated or doped with an alkali metal or alkaline earth metal compound for use in the conversion of synthesis gas and/or in the dehydrogenation of alkylaromatics to alkenylaromatics. Any one or more of the transition metals or compounds can be utilized such as the metals of Groups IB, IIB IIIB, IVB, VB, VIB, VIIB and VIII of the Periodic Table. Suitable metals include zinc, cadmium, copper, silver, chromium, molybdenum, scandium, tungsten, manganese, titanium, rhenium, iron, cobalt, nickel, ruthenium, rhodium, palladium, osmium, iridium, vanadium, platinum, etc. These metals can be present in a concentration of from 0.01 to 30% by weight of the copper aluminum borate catalyst or copper on aluminum borate. These metals or metal compounds can be applied as salts, oxides, etc. and if desired, thermally decomposed to give the corresponding metal or oxides.

While it is not clear at this point whether copper aluminum borate or copper on aluminum borate or combination of the two is the true catalyst in all dehydrogenation reactions and reactions employing a reducing gas, it has generally been found that the induction period for carrying out these reactions is reduced by treating the copper aluminum borate with a reducing agent prior to the desired reaction. A particularly useful method of conditioning a catalyst prior to use or for regeneration of a used catalyst comprises sequentially treating the copper aluminum borate and/or copper on aluminum borate with oxygen containing gas followed by a reducing agent, such as carbon monoxide or hydrogen, sequentially two or more times. At this point, it appears that it is immaterial whether or not the oxidation is carried out prior to or after the reduction step and in fact, the calcination step which is generally carried out using air can be viewed as an oxidation step. However, it is preferred that the sequence ends with a reduction step.

EXAMPLE I

After 12.36 grams of boric acid was dissolved in 160 grams of water contained in a 600 ml beaker by heating on a hot plate, 24.15 grams of copper nitrate [Cu(NO$_3$)$_2$.3H$_2$O] was dissolved. To the warm solution was added 15.3 grams of gamma alumina (surface area 297 m²/g; pore volume, 1.03 cc/g; average pore diameter, 139Å) and after 10 minutes the supernatent liquid was poured off. The wet alumina was left in the container (600 ml beaker) which was placed in a vacuum oven at room temperature to dry. The temperature was raised to about 72° C. and after a total of 17 hours the beaker was removed. The supernatent liquid which had been reheated to dissolve the solids was returned to the beaker with the alumina. After contacting the alumina the liquid was again poured off. This procedure of contacting solution with alumina, decanting supernatent solution and drying alumina was carried out five times including initial contacting. After the fifth drying 50 ml distilled water was added to the solid to help drive the soluble solids into the porous alumina. About 10 ml remaining water, which was very light blue in color, was poured off and the solid dried to 112° C. in the vacuum oven. Nearly equal portions of the dried solid were calcined at three different temperatures namely, 500° C., 830° C. and 925° C. The weight loss at 500° C. was 19.6% and at 830° C. was 20.7%. X-ray diffraction of the material calcined at 500° C. was shown to be amorphous whereas the green solids obtained by calcining at 830° C. and 925° C. was highly crystalline and had the X-ray diffraction pattern for Cu$_2$Al$_6$B$_4$O$_{17}$ set forth in Table I. The surface area and pore properties of the materials are given in Table II.

TABLE II

| Calcination Temperatures | BET Surface Area, M²/g | Pore Volume, cc/g | Average Pore Radius, Å |
|---|---|---|---|
| 830 | 19 | .1639 | 293 |
| 925 | 7 | .0402 | 334 |

The copper aluminum borate calcined at 830° C. was tested under TPR conditions with hydrogen and started to be reduced at about 175° to 200° C., had a peak at 425°–550° C. and 95% of the theoretical amount of hydrogen had reacted by the time the temperature reached 550° C. The reduced material was copper colored.

The copper aluminum borate calcined at 925° C. was tested under TPR conditions with hydrogen, started to be reduced at about 246° C., had a broad peak and the theoretical amount of hydrogen was consumed by the time the temperature reached 700° C. The reduced material was copper colored.

The copper aluminum borate calcined at 830° C. was tested in the oxidative dehydrogenation of butane in the following manner. A quartz tube mounted vertically in a tube-furnace was filled with 4 grams copper aluminum borate. The feed was n-butane in air, which was premixed when it contained about 1% n-butane but at higher concentrations the n-butane in air was fed thru mass-feed controllers to obtain steady flow. Analyses of gases were made on a Fisher-Hamilton gas partitioner using columns with 13X molecular sieve and 30% bis-2-ethoxyethyl sebacate on chromosorb. The reactions were carried out at atmospheric pressure. Table III presents the conditions for and results of the oxidation reaction when using 4.0 grams of preparation calcined at 830° C. It is evident that the solid is serving as an oxydehydrogenation catalyst to produce butenes and 1,3-butadiene. The conditions of oxidation and the results are set forth below in Table III.

TABLE III

OXIDATION OF n-BUTANE OVER COPPER ALUMINUM BORATE
4.0 g Catalyst

| Temp. °C. | Gas Flow Rate, cc/min | Conc. n-Butane mole % | Conv. mole % | $C_4H_8 + C_4H_6$ in Effluent Gas, mole % | Selectivity, mole % | | | |
|---|---|---|---|---|---|---|---|---|
| | | | | | $C_4H_8$ | $1,3-C_4H_6$ | $C_2H_4$ | $CO_x$ |
| 334 | 78 | 34 | 3 | 0.7 | 53 | 15 | 2 | 30 |
| 359 | 78 | 34 | 6 | 1.1 | 44 | 16 | 2 | 38 |
| 360 | 78 | 34 | 6 | 1.1 | 44 | 15 | 4 | 36 |
| 360 | 75 | 17 | 8 | 0.6 | 28 | 14 | 2 | 57 |
| 418 | 75 | 17 | 19 | 0.7 | 20 | 11 | 6 | 63 |
| 345 | 193 | 1.09 | 9 | .06 | | 58 | | 42 |
| 399 | 223 | 1.06 | 19 | .07 | | 40 | | 60 |

EXAMPLE II

This Example illustrates that (1) substantially fully reduced copper aluminum borate (finely divided copper on aluminum borate support) has a different X-ray diffraction pattern from its unreduced precursors, (2) it is a poor oxidation catalyst for aromatics and (3) it is an excellent dehydrogenation catalyst for alkyl substituted aromatics having at least two carbon atoms in at least one alkyl group.

A hot solution of 23.16 g boric acid in 240 ml distilled water was added to 297.16 g of alumina sol (9.73 wt. % $Al_2O_3$ at 500° C.) in a Waring blender. To 37.35 g of copper acetate were added 100 ml distilled water and 30 ml conc. $NH_4OH$. This brought nearly all of the solid into solution and was added to the blender. An additional 30 ml conc. $NH_4OH$ was added to the small amount of remaining solid which was then transferred to the blender. One hundred ml distilled water was used to transfer all remaining material to the blender. After each of these additions the mixture was thoroughly mixed and the final product was spread out to dry for eight days before drying in a vacuum oven to 90° C. This product (II-1) was then calcined at 820° C. for three hours and had a surface area of 54 m²/g, a pore volume of 0.2663 cc/g and an average pore radius of 92A. Under Temperature Programmed Reduction conditions the copper aluminum borate started to be reduced with hydrogen at 220° C., had two broad peaks between 267° to 380° C. and 510° to 566° C. and was substantially completely reduced at 694° C.

The copper aluminum borate was loaded into a ⅜" quartz reactor tube and placed in a Lindberg furnace. The reactor system was equipped with regulators for controlling nitrogen flow and a syringe pump for controlling liquid flows. The liquid was vaporized in a "preheat" section of the reactor and mixed with nitrogen before contacting the catalyst. The reactor effluent was fed into a 10 port gas sampling valve through heated lines. On a signal from the gas chromatograph, an 0.1 cc sample of the reactor effluent was injected into a Perkin-Elmer Sigma 2B Gas Chromatograph. A series of columns and splitters allowed the analysis of both inorganic gases (TC detector) and organics (FID) simultaneously.

Initially, a 4.7 cc bed of the catalyst was used and mesityl oxide was injected into the system with 5% oxygen using a nitrogen diluent gas at a temperature of 200° C. Over a period of about 4 to 5 hours the temperature was raised gradually to 500° C. when the catalyst coked up badly. The catalyst was decoked with 5% oxygen in nitrogen for about 1 hour. Paraxylene was then substituted for the mesityl oxide and was fed to the reactor. Over a period of 3 to 4 hours the temperature was increased from about 200° to 500° C. without oxidation taking place. Then para-cymene was used to replace the paraxylene and the temperature was increased to 600° C. over a period of several hours using a Liquid Space Velocity (LSV) 0.1 (Hr$^{-1}$) resulting in a 92% conversion of the paracymene, yielding a selectivity of 10% to para methyl-alpha methylstyrene. As soon as oxygen was deleted from the feed, conversion dropped to about 83% and selectivity to paramethyl-alpha methylstyrene increased to 90%.

The next day the reactor was started up again except that paraethyltoluene was fed to the reactor with nitrogen for 4 hours at 600° C. using a 0.1 LSV (Hr$^{-1}$) and 1000 GSV (Hr$^{-1}$) (determined at 1 atm+25° C.). Periodic samples indicated that the conversion ranged from about 49 to 53.9% with selectivity ranging from 87 to 92% to paravinyltoluene. The next day the paraethyltoluene run was repeated over a period of 8 hours except using a 0.50 LSV. The percent conversion dropped to about 22 to 27% and the selectivity increased to about 92 to 96%. The next day the run was repeated with essentially the same results. The next day ethylbenzene was used in place of the paraethyltoluene using 0.5 LSV (Hr$^{-1}$) and a 600 GSV (Hr$^-$) resulting in percent conversion ranging from about 19 to 38% with selectivity of from 64 to 84% styrene. During this period the process was permitted to run overnight for 16 hours. The used copper colored catalyst is described below as II-2.

A fresh sample of copper aluminum borate (II-1) was used to replace II-2 and a 3.3 cc catalyst bed was prepared. Cumene and nitrogen diluent was fed to the catalyst for several days varying the conditions as set forth below in Table IV. The run numbers refer to various sampling points.

TABLE IV

| Sample No. | Temp. (°C.) | LSV (Hr$^{-1}$) | GSV (Hr$^{-1}$) | Conversion | Selectivity | Time After Startup |
|---|---|---|---|---|---|---|
| 1 | 600 | 0.50 | 740 | 70.7 | 82.9 | |
| 2 | 650 | 0.96 | 450 | 77.9 | 67.7 | |
| 3 | 550 | 0.14 | 450 | 40.4 | 90.0 | |
| 4 | 650 | 0.14 | 2100 | 91.1 | 75.2 | |
| 5 | 650 | 0.96 | 2100 | 77.4 | 74.2 | |
| 6 | 600 | 0.50 | 740 | 56.9 | 84.3 | |
| 7 | 550 | 0.14 | 2300 | 27.7 | 81.6 | |
| 8 | 550 | 0.96 | 2300 | 9.9 | 83.4 | |
| 9 | 550 | 0.96 | 500 | 19.8 | 74.5 | |
| 10 | 650 | 0.14 | 400 | 80.0 | 68.9 | |
| 11 | 600 | 0.50 | 740 | 56.5 | 85.1 | |
| 12 | | | | 42.9 | 90.0 | 9 hrs. |
| 12A | | | | 44.8 | 89.7 | 24 hrs. |
| 13 | 600 | 0.50 | 740 | 54.6 | 84.7 | |
| 14 | 600 | 1.37 | 700 | 41.3 | 82.6 | |
| 15 | 675 | 0.50 | 700 | 79.5 | 65.4 | |
| 16 | 525 | 0.50 | 700 | 10.2 | 93.7 | |
| 17 | 600 | 0.50 | 740 | 51.6 | 86.3 | |
| 18 | 600 | 0.10 | 700 | 75.9 | 87.3 | |
| 19 | 600 | 0.50 | 3100 | | | Data lost due to valve failure |
| 20 | 600 | 0.50 | 400 | 64.9 | 75.8 | |
| 21 | 600 | 0.50 | 740 | 51.1 | 84.9 | |
| 22 | | | | 38.1 | 89.8 | 32 hrs. |
| 23 | | | | 39.9 | 89.6 | 48 hrs. |
| 24 | | | | 37.2 | 89.5 | 53 hrs. |
| 25 | | | | 36.8 | 89.0 | 73 hrs. |
| 26 | | | | 36.9 | 88.9 | 74 hrs. |

This procedure was carried out for approximately 6 weeks varying the conditions. The copper colored catalyst at this point (II-3) was removed from the reactor and comprised finely divided copper on aluminum borate. Each of the catalyst samples, copper aluminum borate (II-1) and finely divided copper on aluminum borate (II-2 and II-3), was run under the X-ray diffraction conditions referred to above. The strongest line for the copper aluminum borate was 5.29 and the strongest line for the copper on aluminum borate was 2.09 or 2.08 (the copper metal line). In order to make the data more readily comparable, 5.28 and 5.29 were selected as 100%. The X-ray diffraction patterns of these materials is set forth below in Table V.

TABLE V

| dA | II-1 I/I$_o$ | II-2 I/I$_o$ | II-3 I/I$_o$ |
|---|---|---|---|
| 7.46 | 13 | | |
| 5.29 | 100 | 100 | |
| 5.28 | | | 100 |

TABLE V-continued

| dA | II-1 I/I$_o$ | II-2 I/I$_o$ | II-3 I/I$_o$ |
|---|---|---|---|
| 4.99 | 62 | | |
| 4.93 | | 24 | |
| 4.91 | | | 19 |
| 3.73 | 17 | | |
| 3.64 | 9 | | |
| 3.59 | | 12 | 19 |
| 3.35 | | 12 | |
| 3.34 | 14 | | 26 |
| 2.96 | 11 | | |
| 2.84 | 14 | | |
| 2.78 | | 5 | 8 |
| 2.645 | 77 | | |
| 2.64 | | 44 | 38 |
| 2.61* | 20 | | |
| 2.50 | 21 | | |
| 2.46 | | 26 | 42 |
| 2.26 | 30 | | |
| 2.23 | | 12 | |
| 2.22 | | | 17 |
| 2.16 | 39 | | |
| 2.13 | | 47 | 40 |
| 2.09 | | 586 | |
| 2.08 | | | 563 |
| 2.07 | 34 | | |
| 1.98 | 27 | | |
| 1.97 | | 7 | |
| 1.96 | | | 10 |
| 1.91 | | 7 | 8 |
| 1.86 | 19 | | |
| 1.82 | 24 | | |
| 1.81 | | 222 | 217 |
| 1.76 | 9 | | |
| 1.67 | 31 | | |
| 1.66 | | 16 | 19 |
| 1.59 | 11 | | |
| 1.56 | 10 | | |
| 1.55 | | 15 | 18 |

*2.61 was a shoulder on 2.645

The above data clearly shows that the copper aluminum borates of this invention are reduced to substantially zero valent copper on an aluminum borate support or matrix and that both copper aluminum borate and copper on aluminum borate substrates are excellent dehydrogenation catalysts for alkyl substituted aromatics having at least two carbon atoms in at least one alkyl chain.

EXAMPLE III

This Example illustrate the production of copper aluminum borate using an alumina sol and illustrates that surface area of the copper aluminum borate can be varied by controlling NH$_4$OH concentration. The more NH$_4$OH, the higher the surface area. A solution of 44.86 grams [Cu(NO$_3$)$_2$.3H$_2$O] in 50 ml water was added to a 1000 ml beaker containing 300.04 grams of 9.4% by weight alumina sol and mixed with a spatula. A hot solution of 22.96 grams H$_3$BO$_3$ in 225 ml distilled water was added to the copper containing sol followed by further hand stirring of the thick mass. Then 57 ml of concentrated ammonium hydroxide in 500 ml distilled water was added in two portions. The very stiff mass became softer on hand mixing and acquired a uniform blue color. The preparation was next dried by raising the temperature stepwise to 200° C. in a muffle furnace. Some of the product was found scattered about the furnace upon completion of the drying. It was then calcined at 830° C. for 5 hours. The green solid (III-1) had a BET surface area of 18 square meters per gram, a pore volume of 0.1103 cc/g, and an average pore radius of 63Å.

The procedure was repeated except that after the copper nitrate and boric acid additions, the preparation was divided into two nearly equal portions. To one portion the ratio of ammonium hydroxide was doubled (the same 57 ml for one-half the preparation) whereas no ammonium hydroxide was added to the other portion. The two samples were dried in a vacuum oven at 100° C. and then calcined in a muffle furnace at 830° C. for 5 hours. The copper aluminum borate prepared from the doubled portion of ammonium hydroxide (III-2) had a surface area of 29 meters squared per gram, pore volume of 0.1290 cc/g and an average pore radius of 64Å. The surface area of this sample was substantially greater than the surface area in the product of Example III-1 but the average pore radius was approximately the same as that of III-1. The sample prepared without any ammonium hydroxide had too low a surface area to be detected by the nitrogen adsorption method. When a sample of the ammonium hydroxide treated material (III-2) was calcined at 750° C. for 30 minutes the surface area and pore volume were larger but the pore radii smaller than the sample calcined at 830° C. Specifically, the copper aluminum borate calcined at 750° C. had a BET surface area of 66 square meters per gram, pore volume 0.190 cc/g and an average pore radius of 37Å.

EXAMPLE IV

To a hot solution of 45.06g $Al(NO_3)_3.9H_2O$ in 100 ml distilled water in a 250 ml beaker was added 4.98g solid boric acid and then 9.68g of solid $Cu(NO_3)_2.3H_2O$. The pH was 1.6 when conc. ammonium hydroxide addition was started. The mixture gelled after addition of 27.2 ml at a pH of 3.7. The beaker was left covered for 24 hours, the contents were then spread out to dry for 24 hours and next vacuum dried at 99° C. The preparation was next calcined at 420° C. for 0.5 hour (IV-1) and then at 775° C. for 2.5 hours (IV-2). A portion of IV-2 was calcined to 845° C. for 3 hours (IV-3). The portion calcined at 775° C. had a surface area of 92 m²/g, 0.3236 cc/g pore volume and 47Å average pore radius. The portion calcined at 850° C. had a surface area of 43 m²/g, 0.1847 cc/g pore volume and 61Å average pore radius.

EXAMPLE V

This preparation was a five fold scale-up of preparation IV using a 1000 ml beaker and an electric motor driven stirrer blade. To a hot solution of 225.30g of $Al(NO_3)_3.9H_2O$ in 500 cc distilled water was added 24.94g solid boric acid followed by 48.40g $Cu(NO_3)_2.3H_2O$. The pH was 1.4 when dropwise addition of conc. ammonium hydroxide was started. After 1 hour and 25 min. 100.5 ml had been added and pH was 3.2. Addition was continued with a 1 to 1 solution of conc. $NH_4OH$ and distilled water. After 46.5 ml had been added, pH was 3.9 and the mixture was very viscous. It set to a gel in about 5 minutes. The beaker was left covered for 24 hours, the contents were spread out to dry for 4 days and then vacuum dried at 100° C. A portion of this product was next calcined at 420° C. for 0.5 hour (V-1). Portions of V-1 were then calcined at 680° C. (V-2), at 730°–735° C. (V-3), and at 775° C. (V-4). The portion calcined at 680° C had a surface area of 241 m²/g, a pore volume of 0.5894 cc/g and an average pore radius of 33Å. The portion calcined at 730°–735° C. had a surface area of 170 m²/g, a pore volume of 0.4960 cc/g and an average pore radius of 38Å. The portion calcined at 780° C. had a surface area of 103 m²/g, a pore volume of 0.3449 cc/g and an average pore radius of 44Å.

EXAMPLE VI

This preparation starts from dry components using Catapol SB alumina, a product from Conoco which consists of 74.7 wt. % $Al_2O_3$. In a 400 ml mortar were mixed 27.58g Catapol SB (0.2 moles $Al_2O_3$), 32.21 g $Cu(NO_3)_2.3H_2O$ (0.133g atoms Cu), and 16.49g boric acid (0.267g atoms B). To this was added portionwise 84 ml dilute nitric acid (63 ml distilled water +21 ml conc. $HNO_3$) with mixing by spatula until a uniform stiff paste was obtained. After storage overnight covered, the paste was divided into two equal portions. One portion was spread out to dry, while the other portion was treated with 0.5 ml additions of conc. ammonium hydroxide until 15 ml had been added and the pH was 3.7. This was stored overnight in a covered jar and spread out to dry. The two portions were then vacuum dried at 102° C. and both were calcined to 425° C. for 0.5 hour (VI-1, no $NH_4OH$; VI-1N, with $NH_4OH$). Both preparations (VI-1 and VI-1N) were then calcined at 775° C. for 2.5 hours (VI-2 and VI-2N).

EXAMPLE VII

In this preparation PHF alumina sol was used in a procedure similar to that used for aluminum nitrate. To 300.75g of sol (9.60% $Al_2O_3$) with 150 ml distilled water was added 23.34g of boric acid and 45.61g of $Cu(NO_3)_2.3H_2O$ while heating and stirring. A solution of 1 vol. conc. ammonium hydroxide to 1 vol. distilled water was added to this until mixture became very stiff. This required only 6.0 ml giving a pH of 3.2. After leaving the gel covered for 1 day, the stiff gel was cut up and spread to dry for four days, then vacuum dried to 100° C. and calcined to 425° C. for 0.5 hours. This product was then calcined to 775° C. for 2.5 hours (VII-1).

EXAMPLE VIII

This Example illustrates the use of the catalyst prepared in Examples IV thru VII in syn gas conversion. In each case the catalyst was placed in a glass liner which was then inserted into a 500 ml stainless steel autoclave and the autoclave was closed. The vessel was flushed with syn gas and then pressured to 1200–1500 psig depending on cylinder pressure. The vessel was then heated to reaction temperature. The autoclave was left overnight or longer (for example, over a weekend) and the pressure noted. A gas sample was taken and the vessel was depressured through a trap cooled by dry ice. The volume of liquid at room temperature was reported. Also, the presence of solids at dry ice temperature indicated a product predominantly water. Results of the autoclave reactions are set forth in Table VI.

TABLE VI

| | Syn Gas Reaction in 500 cc Autoclave | |
|---|---|---|
| Catalyst | Calcined Temp. °C. | Catalyst Wt., g |
| IV-2 | 775 | 2.0 |
| IV-3 | 845 | 2.0 |
| V-2 | 680 | 2.5 |
| V-3 | 735 | 2.0 |
| V-4 | 775 | 2.5 |
| VI-2N | 775 | 2.5 |
| VII | 775 | 2.5 |

| | Reaction Conditions | | Amt. of |
|---|---|---|---|
| Temp. | Time. | Press (temp). | Liquid |

TABLE VI-continued

| Catalyst | °F. | days | psig × $10^{-3}$ (°F.) | ml |
|---|---|---|---|---|
| IV-2 | 575 | 1 | 1.6(86) — 1.2(575) | 12.1 |
|  | 500 | 1 | 1.6(400) — 1.2(500) | 5.1 |
| IV-3 | 575 | 1 | 1.6(80) — 2.1(575) | 1.8 |
| V-2 | 626 | 2 | 1.6(576) — 1.0(675) | 4.5 |
| V-3 | 575 | 1 | 1.3(83) — 1.7(575) | 1.3 |
|  | 600 | 1 | 1.3(272) — 0.5(298) | 5.8 |
|  | 550 | 1 | 1.2(208) — 0.9(550) | 7.0 |
| V-4 | 575 | 1 | 1.3(93) — 1.2(575) | 8.4 |
| VI-2N | 575 | 3 | 1.3(89) — 1.7(575) | 1 drop |
| VII | 575 | 1 | 1.6(95) — 1.7(575) | 1 drop |
|  | 600 | 1 | 1.6(237) — 2.0(600) | 1 drop |

Usually the catalysts had a black color after the completion of the run.

EXAMPLE IX

Several $Cu_2Al_6B_4O_{17}$ catalysts were tested in a fixed bed, continuous flow pilot plant equipped with on-line gas chromatograph with thermal conductivity detector for CO, $CO_2$ $H_2$, and hydrocarbon analysis. The operating pressure was 500 psi, the gas velocities were 75 to 1500 ml/min, the reaction temperatures were 500 to 650° C., and the catalyst charge was 1.0 to 4.0g. The reactor was a vertical ½" stainless steel tube reactor enclosed in a hinged electrical furnace. The pressure was maintained by a pneumatically operated research control valve. The flow rate was controlled by setting the pressure drop across the reactor with two upstream control valves.

For each catalyst a consistent procedure was followed. One to four grams of catalyst was diluted to 10cc volume with vicor. In order to keep the catalyst bed in the center of the reactor, a supporting bed of vicor mesh was first loaded into the reactor followed by the diluted catalyst and finally be another bed of vicor. The reaction temperature was maintained by three electrical heaters. An internal thermocouple centered in the catalyst bed was used to measure the reaction temperature. The reactor was pressured to 500 psi, and the flow of 2% $CO_2$, 28.3% CO and 69.7% $H_2$ was adjusted to the desired rate. The temperature was then adjusted. When steady state was reached, several successive samples were analyzed by the gas chromatograph. The used catalyst came from the preceding example. The results are set forth below in Table VII.

TABLE VII

| Catalyst | Temp., °F. | CO Conv., % | GHSV, ml hr$^{-1}$ g cat$^{-1}$ | Consumption Ratio, CO/H$_2$ | Composition of Effluent, % |  |  |  | Productivity, g/hr/g cat |
|---|---|---|---|---|---|---|---|---|---|
|  |  |  |  |  | MeOH | DME | CO$_2$ | CH$_4$ |  |
| Fresh IV-2 | 574 | 25.6 | 4500 | 1.0/1.42 | 11.2 | 70.1 | 14.4 | 4.7 | .47 |
| Used IV-2 | 508 | 47.3 | 2050 | 1.0/1.14 | 7.4 | 49.3 | 39.5 | 3.8 | .37 |
| Used V-3 | 567 | 48.1 | 2370 | 1.0/1.14 | 7.4 | 48.0 | 39.4 | 5.2 | .32 |

Each of the catalysts had a black color after the completion of the run.

EXAMPLE X

A hot solution of 23.73g of boric acid in 250 ml distilled water was added to 307.1 g of alumina sol (9.56 wt.% solids by calcining at 500° C.) in a blender while mixing. To this were added 46.30g copper nitrate [Cu(NO$_3$)$_2$.3H$_2$O] dissolved in 50 ml distilled water. Then 60 ml conc. ammonium hydroxide were added and the resulting mixture was blended until uniform and smooth. The product was spread out to dry overnight and was then dried in a vacuum oven at 130° C. A portion of the vacuum-dried product was calcined at 830° C. for about three hours. This product is estimated to contain 1.5 wt.% excess alumina.

EXAMPLE XI

A hot solution of 26.32g boric acid in 260 ml distilled water was added to 306.56g of alumina sol (9.56 wt.% solids) in a blender while mixing. To this was added a solution of 51.40g copper nitrate [Cu(NO$_3$)$_2$.3H$_2$O] and 15.77g chromium acetate [Cr(C$_2$H$_3$O$_2$)$_3$.H$_2$O] in 110 ml distilled water. After thorough mixing, 61 ml of conc. ammonium hydroxide were added. Mixing was continued until a smooth and uniform product was obtained. It was spread out to dry for five days and then dried in a vacuum oven at 130° C. A portion of the vacuum-dried product was calcined at 765° C. (XI-1). Copper chromite was also detected by X-ray diffraction. Assuming no chromium is incorporated in the copper aluminum borate structure and the chromium is completely converted to copper chromite, the final preparation contains 11.2 wt.% $CuCr_2O_4$.

EXAMPLE XII

These preparations were performed as in Example XI except that stoichiometric amounts of ingredients for $Cu_2Al_6B_4O_{17}$ with 22.4 and 11.2 wt% $CuCr_2O_4$ were provided. Thus, for the 22.4 wt.% copper chromite the quantities used were: 299.18g alumina sol (9.73 wt.% solids at 500° C.), 23.53g boric acid dissolved in 250 ml distilled water, 62.82g copper nitrate dissolved in 60 ml distilled water, 35.42g chromium acetate dissolved in 90 ml distilled water and 70 ml conc. ammonium hydroxide. The product was air-dried overnight and vacuum-dried at 110° C. A portion of this product was calcined in two steps. In the first step, the product was heated to 410° C. and then was heated to 780° C. for three hours in the second step (XII-1). The product with 11.2 wt.% $CuCr_2O_4$ was also calcined in this manner (XII-2).

EXAMPLE XIII

In this preparation, aluminum nitrate was used instead of alumina sol. It was performed in a 1000 ml beaker placed on a hot plate and provided with an electric driven paddle stirrer. Aluminum nitrate [Al(NO$_3$)$_3$.9H$_2$O], 225.10g, was dissolved in 475 ml distilled water. To this solution were added 24.73g boric acid, 59.99g copper nitrate [Cu(NO$_3$)$_2$.3H$_2$O], and 38.67 g chromium nitrate [Cr(NO$_3$)$_3$.9H$_2$O]. The pH of this black solution was 1.3 when dropwise addition of conc. ammonium hydroxide was started. After 39 minutes, 80 ml had been added and the pH was 2.8. Addition was continued with a 1 to 1 solution of conc. NH$_4$OH in distilled water. After 70 minutes, 87.5 ml had been added, the pH was 3.7, and the product was a stiff gel. The beaker was left covered for 24 hours, the contents were spread out to dry for two days and then was vacuum-dried at 105° C. A portion of this product was calcined at 430° C. (XIII-1). A portion was next calcined at 730° C. for three hours (XIII-2) and another portion was calcined at 770° C. for three hours (XIII-3).

TABLE VIII

| Example No. | Surface Area, M²/g | Pore Volume, cc/g | Avg. Pore Radius, Å |
|---|---|---|---|
| XI-1 | 47 | .153 | 41 |
| XII-2 | 44 | .213 | 69 |
| XIII-2 | 112 | .216 | 22 |
| XIII-3 | 46 | .113 | 30 |

EXAMPLE XIV

This example illustrates hydrogenation of diethylsuccinate to obtain butanediol using either copper aluminum borate as the hydrogenation catalyst or copper aluminum borate/copper chromite. Hydrogenations were carried out by purging a 1-liter 316 SS autoclave with 150 grams diethylsuccinate, 450 grams ethanol and a powdered catalyst. Hydrogen was admitted to the reactor to maintain a pressure of 2000 psig. The temperature was maintained at 200° C. The results are set forth below in Table IX.

TABLE IX

| Catalyst | Weight of Catalyst (grams) | Hydrogenation Rate (mole fraction/min.) |
|---|---|---|
| Example X | 9.0 | $0.79 \times 10^{-3}$ |
| Example XI-1 | 8.2 | $1.58 \times 10^{-3}$ |

EXAMPLE XV

This example illustrates the conversion of dimethylsuccinate to butanediol using a copper chromite commercial hydrogenation catalyst and copper aluminum borate catalysts containing the indicated concentrations of copper chromite. The reactions were carried out by charging the reactor with 40 grams dimethylsuccinate, 120 grams methanol and 4 grams of powdered catalyst. The hydrogenation was carried out at 200° C., 1800 psig for 6.5 hours. The results are set forth below in Table X.

TABLE X

| Catalyst | % Copper Chromite | % DMS² Conversion | Selectivity (%) | | | |
|---|---|---|---|---|---|---|
| | | | GBL | BDO | MHB | MHBS |
| Strem - barium promoted copper chromite 29-041 | 100% | 38.7 | 19.0 | 57.4 | 15.8 | 7.8 |
| Example XII-1 | 22% | 34.0 | 22.6 | 52.6 | 18.3 | 6.5 |
| Example XII-2 | 11% | 28.4 | 39.8 | 40.6 | 14.8 | 4.8 |
| Example XIII-2 | 15.6% | 21.0 | 50.8 | 7.1 | 42.1 | Low |
| Example XIII-3 | 15.6% | 18.0 | 50.7 | 30.9 | 18.4 | Low |

²DMS = dimethylsuccinate
GBL = gamma-butyrolactone
BDO = 1,4-butanediol
MHB = methyl-4-hydroxybutyrate
MHBS = methyl(4-hydroxybutyl)succinate

EXAMPLE XVI

A hot solution of 21.63g boric acid in 225 ml distilled water was added to 294.44g of alumina sol (27.03g alumina on a dry solids basis) in a blender while mixing. To this was added 31.43g copper acetate and 4.35g nickel acetate in 50 ml distilled water and 38 ml concentrated ammonium hydroxide. The solid salts remaining in the beaker was dissolved in 20 ml concentrated ammonium hydroxide and added to the blender. The beaker was then rinsed with distilled water and added to the blender. The stiff mixture was worked with a spatula and the blender action until a smooth gel was produced. The gel was transferred into plastic dishes for drying. After three days, the solids were transferred to two petri dishes and vacuum dried for 48 hours (0.25 atm, 50° C. initial temperature and 106° C. final temperature). Sixteen and seventeen hundredths g of the dry solids were calcined by heating from 115° C. to 260° C. for a 2 hr period, held at 260° for 1 hr, from 260° C. to 820° C. over a 3 hr period, held at 820° for 3 hrs and then cooled to 110° C. X-ray diffraction data indicated that the material was highly crystalline and had only a single component. The copper (90) nickel (10) aluminum borate had a surface area of 36 square meters per gram, 0.1289 ccs per gram pore volume and an average pore radius of 43Å.

EXAMPLE XVII

Example XVI was repeated except that the concentration of copper acetate and nickel acetate was changed to 27.94g copper acetate and 8.71g nickel acetate. The copper (80) nickel (20) aluminum borate was highly crystalline and the crystals appeared to be homogeneous. The copper nickel aluminum borate had a surface area of 31 square meters per gram, a pore volume of 0.1100 cc/g and an average pore radius of 37Å.

EXAMPLE XVIII

A hot solution of 23.05g boric acid in 240 ml distilled water was added to 310.94g alumina sol (28.52g dry solids basis) in a blender while mixing. To this were added 40.54g copper nitrate and 5.55g zinc nitrate in 50 ml distilled water. Concentrated ammonium hydroxide (60 ccs) was then added and the mixture blended using a spatula until it was very smooth. The gel was placed on a tray and allowed to dry in air for 48 hrs and then dried under vacuum at 91° C. A portion of this solid was calcined at 380° C. to decompose nitrates and then at 825° C. for 3 hours. The copper (90) zinc (10) aluminum borate was highly crystalline and X-ray diffraction indicated that it was homogeneous. The material had a surface area of 35 square meters per gram, 0.1411 cc/g pore volume and an average pore radius of 59Å.

EXAMPLE XIX

Example XVIII was repeated except that the copper nitrate and zinc nitrate concentrations were changed to 35.95g copper nitrate and 11.07g zinc nitrate. The copper (80) zinc (20) aluminum borate was highly crystalline and homogeneous. The material had a surface area of 33 square meters per gram, 0.1355 cc per gram pore volume and an average pore radius of 59Å. A sample calcined at 730° C. had a surface area of 72 square meters per gram, 0.1858 ccs/g pore volume and an average pore radius of 33Å.

EXAMPLE XX

This example illustrates the preparation of $K_2O$/$MoO_3$/$CeSO_4$ doped copper aluminum borate and the use thereof for dehydrogenation of para-ethyltoluene. Into a blender was placed 79.36 g $K_2CO_3$, 97.22 g $Cu(NO_3)_2 \cdot 2\frac{1}{2} H_2O$, 51.74 g $H_3BO_3$, 177.30 g $Al(NO_3)_3 \cdot 9 H_2O$, and 70 ml of water. The blender was turned on and after the foaming subsided, another 100 ml of water was added, yielding a clear blue solution. Upon standing overnight, concentrated ammonium hydroxide was added in three stages: 40 ml, 55 ml, and 30 ml with stirring. The material gelled after the third addition of concentrated ammonium hydroxide and was dried, yielding 480g of material.

To 20.65g of the air dried material prepared in the preceding paragraph was added 30 ml of an aqueous solution containing .19g $(NH_4)_6Mo_7O_{24}.4H_2O$ (2% by weight $MoO_3$ based on doped catalyst) and 50 ml of an aqueous solution containing 0.282g $Ce_2(SO_4)_6.8H_2O$ (about 2% by weight Ce based on doped catalyst). The mixture was stirred intermittently and allowed to air dry. The solid residue was heated to 800° C. over 5 hours, held at 800° C. for 1 hr and allowed to cool down overnight in the oven.

The doped copper aluminum borate catalyst prepared in the preceding paragraph was ground to 18 to 40 mesh and used in the dehydrogenation of ethylbenzene and p-ethyltoluene in the manner described in Example I. The ethylbenzene runs were carried out at a 0.9 liquid hour space velocity, 620° C. temperature, steam:ethylbenzene molar ratio of 20:1, yielding 42% conversion and 72% selectivity to styrene. The p-ethyltoluene conversion to p-methylstyrene was carried out using a 0.2 liquid hour space velocity, 620° C. temperature, 15:1 molar ratio of steam to p-ethyltoluene, a 5:1 toluene to p-ethyltoluene dilution, yielding 68% conversion and 93% selectivity to p-methylstyrene.

EXAMPLE XXI

This example illustrates the dehydrogenation of cumene and p-ethyltoluene using a diluent comprising steam and nitrogen. Three and three-tenths grams of the catalyst prepared in Example II, ground to 18 to 40 mesh, was employed in the reactor described in Example II. Initially p-ethyltoluene was flowed into the reactor at 0.38 liquid hour space velocity, 11:1 diluent to p-ethyltoluene ratio (8:1 steam and 3:1 nitrogen) at 588° C., yielding a relatively poor conversion and selectivity. The catalyst was decoked with 5% oxygen and nitrogen for about 1 hr. Cumene was then run at 0.38 liquid hour space velocity, 11:1 diluent ratio (8:1 steam and 3:1 nitrogen) at 588° C. providing 40% conversion to alphamethylstyrene and 88% selectivity. The feed was then switched from cumene to p-ethyltoluene using the same diluent dilution and conditions providing 22% conversion to p-methylstyrene and 93% selectivity. Conditions were then changed to 0.72 liquid hour space velocity, 10:1 diluent ratio for the p-ethyltoluene (8:1 steam and 2:1 nitrogen) at 598° C., yielding 40% conversion and 92% selectivity to p-methylstyrene.

EXAMPLE XXII

This example illustrates conversion of cumene to alphamethylstyrene using a 20:1 diluent ratio and a copper aluminum borate catalyst having a BET surface area of 32 square meters per gram, 0.198 cc per gram pore volume and 98 Å average pore radius. The catalyst was prepared in the same manner as the catalyst prepared in Example II except that the concentration of concentrated ammonium hydroxide was reduced from 60 to 30 ml. After the catalyst was ground to 18 to 40 mesh, 3.85 g (3.8 cc) was placed in the reactor. The dehydrogenation was run using a 20:1 diluent ratio (17:1 steam and 3:1 nitrogen) at 0.81 liquid hour space velocity at 600° C., yielding 46% conversion and 92% selectivity to alphamethylstyrene.

EXAMPLE XXIII

This example illustrates the preparation of a copper aluminum borate/copper chromite catalyst and the use thereof in the dehydrogenation of p-cymene, p-ethyltoluene and cumene. Into a blender was placed 300.77g of an alumina sol (9.73 dry wt.% $Al_2O_3$, 0.2869 moles $Al_2O_3$) and 23.64g boric acid (0.38 moles) dissolved in 250 ml of water. A copper nitrate/chromium acetate solution was prepared by dissolving 53.34g copper nitrate (0.22 moles) in 60 ml water and adding thereto a solution of 15.56g chromium acetate in 70 ml distilled water. On heating, the copper nitrate/chromium acetate solution became dark and opaque. The dark opaque solution was added to the blender and thoroughly mixed before transfer to petri dishes to dry. The petri dishes were placed in a vacuum oven and dried overnight at 55° C. at 20 inches (0.3 atm) vacuum. Over the next two days, the temperature was gradually raised to 106° C. while the vacuum pressure was increased to about 15 inches (0.5 atm), yielding 110.67g of a dark blue solid. A portion of this material (27.09g) was placed in a petri dish and calcined by heating as follows: 120° C. for 0.6 hr, 235° C. for 0.5 hr, 250° C. for 0.5 hrs, 375° C. for 0.8 hr, and then 400° C. After cooling for 1 hr the composition while still at 300° C. was placed in a desiccator overnight. The solid (13.76g) was placed in a small alumina dish and calcined according to the following program: 40° C. for 2 hrs, 500° C. for 1 hr, 500° C. for 1.5 hrs, 735° C. for 3 hrs and then held at 750° C. and cooled. After cooling for 1.2 hrs, the temperature reached 482° C. and the dish was removed from the oven and placed in a desiccator, yielding 13.48g of 11.2% copper chromite in copper aluminum borate.

After grinding to 18 to 40 mesh, 3.7g of the catalyst prepared in the preceding paragraph was placed in a reactor and used in dehydrogenation in the manner described in Example II. The p-cymene runs were carried out at a 0.45 liquid hour space velocity, 592° C. temperature, a steam: p-cymene mole ratio of 20:1, yielding 37% conversion and 31% selectivity. The p-ethyltoluene conversion was carried out using a 0.45 liquid hour space velocity, 588° C. temperature, 15:1 molar ratio of steam to p-ethyltoluene, yielding 32% conversion and 40% selectivity. The cumene conversion was carried out using a 0.94 liquid hour space velocity, 560° C. temperature, a 6:1 molar ratio of diluent to cumene (4:1 steam and 2:1 nitrogen), yielding 47% conversion and 87% selectivity.

EXAMPLE XXIV

This example illustrates the preparation of a copper oxide on aluminum borate substrate and the in situ conversion of the copper oxide to copper in the dehydrogenation of a cumene. Nine grams of aluminum borate $(Al_4B_2O_9)$ was placed into an evaporating dish. One and thirty-nine hundredths grams copper nitrate was dissolved in 6 ml water. The copper nitrate solution was added to the aluminum borate solid until about 4.8 ml solution was absorbed by the solid. The weighed solid was placed in a vacuum oven and the temperature gradually raised to 90° C. The solid was impregnated three additional times with 4.55 ml copper nitrate solution, dried at 97° C., 4.65 ml copper nitrate solution, dried at 98° C. and finally 4.5 ml copper nitrate solution, dried at 106° C., yielding a solid weighing 9.69g. The resulting solid was placed in an alumina dish and calcined as follows: 120° C. for 1.2 hrs, 275° C. for 0.5 hr, 300° C.

for 0.8 hr, 560° C. for 1.0 hr, held at 575° C. and then allowed to cool overnight in a desiccator. The solid weighed 9.31g and was pressed into two large pellets weighing 4.38g and 4.34g respectively.

After grinding to 18 to 40 mesh, 1.938g of the catalyst (3.0 cc) was placed in the reactor described in Example II. The reactor was heated at 670° C. with 50 cc of air flowing over it overnight. The temperature was reduced to 586° C. and after several hours cumene was introduced at a 0.78 liquid hour space velocity, 7.6 moles of steam per mole of cumene, and 2.0 moles of nitrogen per mole of cumene. Conversion to alpha-methyl styrene is set forth in the table below:

TABLE XI

| Hours On Stream | Percent Conversion | Percent Selectivity |
| --- | --- | --- |
| 3.0 | 64.6 | 85.1 |
| 4.0 | 53.0 | 86.2 |
| 19.0 | 47.8 | 74.1 |
| 42.0 | 45.8 | 78.6 |
| 51.0 | 55.7 | 81.7 |
| 67.0 | 49.5 | 83.8 |
| 68.0 | 50.7 | 82.8 |
| 91.0 | 50.0 | 85.0 |
| 94.5 | 54.5 | 81.7 |
| 95.0 | 52.5 | 83.0 |
| 108.0 | 69.4 | 78.4 |
| 114.0 | 50.5 | 83.8 |
| 131.5 | 51.9 | 78.6 |
| 135.3 | 49.2 | 82.5 |

EXAMPLE XXV

This example illustrates that in the absence of copper, aluminum borate ($Al_4B_2O_9$) is a poor dehydrogenation catalyst. The dehydrogenation run described in Example II was repeated using 3.0 cc ground aluminum borate, a liquid hour space velocity of 0.78, a diluent ratio of 10:1 (2:1 nitrogen and 8:1 water) at a temperature of 586° C. Initially the conversion started off high at 97% after three hours but there was only 8% selectivity to methylstyrene. After 65 hours, the conversion dropped to 38% and the selectivity rose to 64%. A repeat run yielded essentially the same results.

EXAMPLE XXVI

This example illustrates the dehydrogenation of cumene to alphamethyl-styrene using the copper (80) zinc (20) aluminum borate (calcined at 825° C.) of Example XIX. Three and two-tenths cc of the catalyst was placed in the reactor of Example II and the dehydrogenation was run in the same manner using a liquid hour space velocity of 0.88, a diluent ratio of 15:1 (8:1 nitrogen and 7:1 steam) at a temperature of 600° C. The conversion to methyl-styrene was approximately 40–45 wt.% and the selectivity was 88–90% but the material was much lighter (nearly colorless) as opposed to the yellow color of other cumene dehydrogenations described above.

EXAMPLE XXVII

This example illustrates the preparation of a large batch of copper aluminum borate and its use in larger scale dehydrogenation reactors using feeds simulating those emanating from an ethylene alkylation of toluene unit. The copper aluminum borate was prepared by (1) adding 400 g $H_3BO_3$ to 3384 ml distilled water and heating to dissolve;.

(2) adding 646.4 g $Cu(OAc)_2 \cdot H_2O$ to 2400 ml water. Heating and stirring to substantially dissolve. After 15 minutes of heating adding one-half (480 ml) 29% aqueous $NH_3$ to speed dissolution of salt;

(3) weighing 6352 g PHF alumina (7.8% solids) to mixer bowl;

(4) adding hot boric acid solution to the PHF alumina in a mixer. Mixing slowly for 1 minute;

(5) adding remaining 480 ml (29% aqueous ammonium hydroxide) ammonia to $Cu(OAC)_2$ solution.

(6) After all solids were dissolved adding the ammoniacal copper acetate solution to the slowly mixing liquid in the blender forming a gel. Increasing the mixing speed and thoroughly mixing the gel for 5 minutes;

(7) removing the smooth uniform consistency gel from the mixer, and spreading to dry on large plastic sheets in layer ⅛" thick, for two days;

(8) collecting the air-dried catalyst (now shriveled into random sized flakes), placing in crystallizing dishes and loading into a vacuum oven under 20" of house vacuum (maintained with $N_2$ bleed) at 45° C. overnight;

(9) raising the vacuum oven temperature 10–20° C. at a time at intervals over a period of two additional days until 100–110° C. is reached;

(10) transferring the vacuum dried catalyst to alumina trays, then placing in a calcining oven at 120° C. Calcination was as follows:

| | |
| --- | --- |
| 120° C.→ | 2 hrs |
| 300° C. | 2 hrs |
| 300° C.→ | 3 hrs |
| 820° C. | 3 hrs |
| 820° C. | >4 hrs |

Eighty cc of the catalyst (18 to 40 mesh) was placed in a large reactor and a feed comprising 92% toluene, 5.8% p-ethyltoluene, 0.8% ethylene and minor amounts of benzene and metaethyltoluene were fed to the reactor at a weight hour space velocity of 0.16 based on the p-ethyltoluene concentration using a diluent ratio of approximately 16:1 based on the p-ethyltoluene (toluene and ethylene diluents) at 1 atm at 630° C. Over a five day period the average conversion of p-ethyltoluene was 29 to 32% with 80% selectivity to p-ethylstyrene.

This procedure was repeated using a larger reactor containing 256 g catalyst and nitrogen as an additional diluent. In this case the feed contained about 9 wt.% p-ethyltoluene. Conversion was carried out using a weight hour space velocity of 0.04 based on p-ethyltoluene, a 45:1 diluent ratio, and 1 atm pressure at 630° C. Over several days the average conversion was 40 to 45% with 90 to 95% selectivity of the p-ethyltoluene to p-methylstyrene.

EXAMPLE XXVIII

This example illustrates the production of copper aluminum borate containing 1% by weight $K_2O$. After 24.94g of boric acid was added with stirring to a cloudy mixture of 225.3g $Al(NO_3)_3$ monohydrate in 500 ml water and heated to form a clear solution, 48.40 g $Cu(NO_3)_2$ trihydrate was added. When the solids dissolved, 100.5 ml of concentrated hydroxide was added dropwise over 1 hr 25 minutes raising the pH from 1.4 to 3.2. Forty-three ml of 1:1 $NH_4OH:H_2O$ solution was added dropwise over 46 minutes raising the pH to 3.85 and forming a viscous composition. An additional 3.5 ml of the ammonium hydroxide was added with stirring raising the mixture to pH 3.9. After blending about 5 to 10 minutes, the mixture set up and the gel was allowed to stand covered for 1 day and then spread out to dry on plastic dishes. After drying, the material was transferred to petri dishes and placed in a vacuum oven and dried by slowly raising the temperature to 89° C. over 6 and ½ hours at approximately 0.27 inches mercury vacuum (0.1 atm). After the dishes were removed from the oven and large pieces of catalyst broken up, the material was returned to the vacuum oven and held at 100° C. and 14 to 20 inches mercury vacuum (0.5 to 0.7 atm) overnight yielding 220g solid. The copper aluminum borate was calcined in two batches at about 400° C. The two batches were combined and calcined by heating to about 740° C. The observed temperatures rose to 772° C.

A solution of 4.0 ml distilled water and 0.1084 g of $KHCO_3$ was added to 5.00 g of the copper aluminum borate by the incipient wetness technique in increments. The solid was dried in a vacuum oven at 110° C. and then calcined at 420° C.

EXAMPLE XXIX

This example illustrates inclusion of 2.0% $K_2O$ in copper aluminum borate during the solution stage of the preparation. To 226.14 g aluminum nitrate in a 1000 ml beaker were added 350 ml distilled water, 24.77 g $H_3BO_3$ and 46.52 g $Cu(NO_3)_2.2\frac{1}{2}$ $H_2O$. While heating on a hot plate with stirring 2.56 g $KHCO_3$ was added portionwise to prevent excessive effervescence. Addition of concentrated $NH_4OH$ to the solution was then started. After 96 ml were added in 30 minutes, 53.8 ml of a 1:1 solution of concentrated $NH_4OH$ and distilled water were added in 20 minutes. The beaker containing the thick gel was covered for 23 hours, the gel was spread out to air dry for 52 hours and the resulting solid was dried in a vacuum oven to 115° C. A portion of this solid was calcined to 420° C. and some of this solid was calcined at 775° C. for 2.5 hours forming a black solid.

EXAMPLE XXX

This example illustrates the production of a copper (75%) magnesium (25%) aluminum borate. To 226.03 g $Al(NO_3).9H_2O$ in a 1000 ml beaker were added 350 ml distilled water, 24.73 g $H_3BO_3$, 12.82 g $Mg(NO_3)_2.6-H_2O$ and 34.89 g $Cu(NO_3)_2.2\frac{1}{2}$ $H_2O$. After these were dissolved by heating while stirring addition of concentrated $NH_4OH$ was started. After 97.2 ml concentrated $NH_4OH$ were added in 39 minutes, 57.3 ml of a 1:1 solution of concentrated $NH_4OH$ and distilled water were added in 22 minutes. The beaker containing the thick gel was left covered for 24 hours, the gel was spread out to air dry for 25 hours and the resulting solid was dried in a vacuum oven to 97° C. A portion of this solid was calcined to 300° C. and a portion of this solid was calcined at 787° C. for 2.5 hours.

EXAMPLE XXXI

This example illustrates the production of a catalyst comprising copper aluminum borate/aluminum borate, for use in dehydrogenation and onstream doping using potassium carbonate. To 225.12 g of $Al(NO_3)_3.9H_2O$ in a 1 liter beaker was added 400 ml distilled water while heating on a hot plate, followed by 22.69 g boric acid and 32.21 g copper nitrate. After the solids dissolved, 61.4 ml concentrated ammonium hydroxide was added raising the pH from 0.2 to 2.5 followed by 115 ml 1:1 concentrated ammonium hydroxide:distilled water raising the pH to 3.4. The mixture set up into a thick gel and allowed to stand overnight. The gel was then spread over three plastic dishes and left to dry in the hood for one week. The solids were then dried in three petri dishes in a vacuum oven for 28 hrs at about 20 inches mercury (0.3 atm pressure). The temperature was gradually raised from room temperature to 77° C. after 4 hrs, 105° C. after 8 hrs, 118° C. after 23 hrs and 136° C. at the end of the 28 hr drying period yielding 207.82 g. The copper aluminum borate/aluminum borate mixture was calcined by heating to 400° C. and then at 750° C. (780° C. observed temperature). The copper aluminum borate/aluminum borate had a BET surface area of 109 square meters per gram, 0.3382 cc per g pore volume and an average pore radius of 47 A. XRD pattern showed both copper aluminum borate and aluminum borate ($2Al_2O_3.B_2O_3$) with the ratio of the 5.3 A to 4.95 A lines being 2.9 although the nominal ratios of reactants indicated that the ratio should be 3.9.

The copper aluminum borate/aluminum borate composition was loaded into a reactor and used in dehydrogenation in the manner described in Example II using 2.9 cc catalyst, 1.8 g. The reaction was run at 580° C., a liquid hour space velocity of 0.81, a mole ratio of steam to cumene of 7.6 and a mole ratio of nitrogen to cumene of 2.0. After 45 hrs on stream the percent conversion dropped from about 71.3% conversion to 46.4% conversion and the selectivity increased from 86.3% to 91.8%. At this point there was a brief temperature runaway with the reactor temperature going to 800° to 850° C., for a short time. When the reactor cooled to 580° C. cumene was again started using the same conditions. During the 24 hr period running from 51 hrs on stream to 75 hrs on stream the percent conversion was substantially lower than the earlier part of the run and was approximately 20.1 to 24.5% with 67.7% to 77.7% selectively. In order to attain improved yields, the catalyst was decoked by adding 161 cc per minute of 7.6% oxygen in nitrogen over the catalyst (no cumene or steam) for 2 hrs at 580° C. Cumene feed was restarted and over the next 48 hrs the percent conversion ranged from about 43.7% to 68.8% with selectivities increase from 44.9% to 92.9%. After 52 hrs on stream 0.1 cc of a solution of 2 cc water and 1 g potassium carbonate was injected into the top of the catalyst bed and cumene dehydrogenation was resumed under the same conditions. Over the next 14 hrs the percent conversion was maintained at 46.6 to 47.8% with selectively at 88.3 to 90%. Since the cumene feed was free of ethylbenzene, the addition of potassium carbonate did not seem to have any effect.

At this point dehydrogenation of ethylbenzene was started using the reactor temperature of 600° C., 0.81 liquid hour space velocity, 6.6:1 steam of ethylbenzene ratio and 1.7:1 nitrogen to ethylbenzene ratio. An injection of 0.1 cc of a 50 wt. % solution of potassium carbonate was added 34 hrs after the beginning of this run. The results are set forth below in Table XII.

TABLE XII

| Time (hrs) | % Conversion | % Selectivity |
| --- | --- | --- |
| 1 | 18 | 93 |
| 3 | 24 | 93 |
| 4 | 28 | 72 |
| 5 | 28 | 85 |
| 6 | 31 | 88 |
| 7 | 75 | 81 |
| 8 | 79 | 89 |
| 11 | 82 | 73 |
| 15 | 85 | 64 |
| 16 | 77 | 80 |
| 27 | 63 | 62 |

TABLE XII-continued

| Time (hrs) | % Conversion | % Selectivity |
|---|---|---|
| 28 | 61 | 64 |
| 32 | 44 | 63 |
| 33 | 57 | 52 |
| 35 | 44 | 61 |
| 38.5 | 38 | 63 |
| 39 | 44 | 61 |
| 51 | 44 | 53 |
| 52 | 41 | 61 |

The above table illustrates that the percent conversion rose dramatically over several hours and was nearly 80% with over 85% selectivity at one point, whereas when ethylbenzene was passed over regular copper aluminum borate without potassium doping there was only minimal conversion (10% conversion at 600° C., 0.83 liquid hour space velocity, 7:1 diluent ratio).

EXAMPLE XXXII

This example illustrates the conversion of syn gas using the doped catalysts of Example XXVIII and XXIX and the Mg containing catalyst of Example XXX using a 500 ml static autoclave. In each case the catalyst was added to the autoclave, which was pressurized at room temperature with a premixed cylinder of syn gas at 1000 to 1500 psi. The reactor temperature was raised to the desired level where the reaction was allowed to proceed overnight (or over the weekend). After approximately 16 hrs a gas sample was taken and analyzed by gas chromatography for light hydrocarbon products. The total reactor gas was vented through a dry ice trap to collect a liquid product. The liquid was also analyzed by gas chromatography. Specifically 2.5 g of the catalyst of Example XXVIII containing 1% $K_2O$ on copper aluminum borate was loaded into the reactor. The conditions of the test run and the results are given below in Table XIII.

TABLE XIII

| Run | 1 | 2 | 3 | 4 |
|---|---|---|---|---|
| Syngas Composition %, $CO/CO_2/H_2$ | 33/2/65 | 33/1/65 | 63/16/36 | 71/1/28 |
| Initial reaction pressure (temp) | 1500(95) | 1500(350) | 1450(600) | 1450(650) |
| Final reaction pressure (temp) | 900(600) | 1325(600) | 1450(650) | 1600(725) |
| Reaction temp., °F. | 600 | 600 | 650 | 725 |
| Reaction time, hrs | 72 | 15.5 | 16 | 22.5 |
| Volume of product, cc | 12 | 3.7 | 7.3 | 1.5 |
| Product Composition, % | | | | |
| MeOH | 98.1 | 91.0 | 91.0 | 63.1 |
| EtOH | — | 4.5 | 2.5 | 4.9 |
| PrOH | .1 | 2.2 | 2.8 | 7.0 |
| nBuOH | 1.8 | .6 | .9 | 6.9 |
| Other | — | 1.7 | 2.8 | 18.1 |

This catalyst made higher molecular weight alcohols and hydrocarbons from syn gas.

Two g of the catalyst of Example XXIX, 2% $K_2O$ in copper aluminum borate, was loaded into the reactor. For all tests with this catalyst the syn gas composition was 33% CO/64% $H_2$/3% $CO_2$.

TABLE XIV

| Run | 1 | 2 | 3 |
|---|---|---|---|
| Initial reaction pressure (temp) | 1000(85) | 1000(100) | 960(110) |
| Final reaction | 755(600) | 885(600) | 990(674) |

TABLE XIV-continued

| Run | 1 | 2 | 3 |
|---|---|---|---|
| pressure (temp) | | | |
| Reaction temp., °F. | 600 | 600 | 725 |
| Reaction time, hrs | 66 | 15.5 | 17 |
| Volume of product, cc MeOH | 7.2 | 6.9 | 5.0 |

Two g of the catalyst of Example XXX, 75% Cu-25% Mg aluminum borate, was loaded into the reactor. The reactor was pressurized with syn gas of 33% CO/64% $H_2$/3% $CO_2$ composition. The reaction temperature was 600° F.

TABLE XV

| Initial pressure (temp) | 1120(77) |
|---|---|
| Final pressure (temp) | 1075(600) |
| Reaction time, hrs. | 17 |
| Volume of product, cc MeOH | 2.0 |

The product from the reaction was methanol with a small amount of dimethyl ether.

EXAMPLE XXXIII

To 226.16 g $Al(NO_3)_3.9H_2O$ in a 1000 ml beaker was added 350 ml distilled water and the mixture was heated on a hot plate with stirring. To this was added 24.75 g boric acid and 46.57 g $Cu(NO_3)_2$ 2½ $H_2O$. To the hot solution was added 97.4 ml concentrated $NH_4OH$ followed by a 1:1 mixture of concentrated $NH_4OH$ and distilled water. A stiff gel formed after 57.4 ml was added. The beaker was left covered for 24 hrs when the stiff gel was spread out to air dry for two days and then dried in a vacuum to 100° C. (XXXIII-1). A portion of this solid was calcined at 425° C. (XXXIII-2) and then at 780° C. (XXXIII-3). Another portion of (XXXIII-2) was wetted with water, formed into two one-inch pellets which were calcined at 793° C. and ground to 14–35 mesh yielding 3 g of copper aluminum borate (XXXIII-4). The fines from the second pellet were repelleted and broken up (XXXIII-5).

EXAMPLE XXXIV

This example illustrates the preparation of 10:3 mole ratio copper aluminum borate/aluminum borate. To 225.14 g of $Al(NO_3)_3.9H_2O$ in a 1000 ml beaker was added 400 ml distilled water and the mixture was heated on a hot plate while stirring. To this was added 23.70 g boric acid and 40.27 g $Cu(NO_3)_2.3H_2O$. After addition of 67.5 ml concentrated $NH_4OH$ to the hot clear solution, a 1:1 mixture $NH_4OH/H_2O$ was added until a stiff gel formed. This required 122.5 ml. The beaker was left covered for 25 hrs when the stiff gel was spread out to air dry and then dried in a vacuum to 100° C. A portion of this solid was calcined at 430° C. Portions of this solid were then calcined at 780° C. (XXXIV-1) and 830° C. (XXXIV-2).

The remaining vacuum dried preparation was calcined at 430° C. This solid was ground, sieved, wetted with water and formed into two one-inch pellets. After vacuum drying, these were calcined at 780° C. (XXXIV-3). The solid was broken up and sieved to 14–35 mesh.

The physical properties of the catalysts prepared in Examples XXXIII and XXXIV are set forth below in Table XVI.

TABLE XVI

| I.D. | Compositions | Surface Area, $m^2/g$ | Pore Vol, cc/g | Avg Pore Radius, Å |
|---|---|---|---|---|
| XXXIII-3 | Cu AB | 95 | 0.344 | 49 |
| XXXIII-5 | Cu AB | 129 | 0.408 | 47 |
| XXXIV-1 | Cu AB/AB | 44 | 0.171 | 65 |
| XXXIV-2 | Cu AB/AB | 134 | 0.432 | 48 |
| XXXIV-3 | Cu AB/AB | 72 | 0.276 | 55 |

EXAMPLE XXXV

This example illustrates conversion of syn gas using catalysts of Examples XXXIII and XXXIV in the flow reactor described in Example IX. The process was carried out in the manner described in Example IX except for the conditions set forth below in Tables XVII and XVIII using 5.0 g, 6.8 cc of copper aluminum borate/aluminum borate (XXXIV-3) in Table XVII and 5.0 g, 8.2 cc copper aluminum borate of Example XXXIII-4 and XXXIII-5 in Table XVIII.

TABLE XVII

| Line | Temp. °C. | GHSV | Press. psig | $H_2/CO$ Molar Ratio | $CO_2$ in Feed Mole % | CO Conv. Mole % | Selectivity of CO to Mole % | | | | Production MeOH, g/g/hr |
|---|---|---|---|---|---|---|---|---|---|---|---|
| | | | | | | | MeOH | $Me_2O$ | $CH_4$ | $CO_2$ | |
| 1 | 344 | 3,900 | 1000 | | | 45 | | | | | |
| 2 | 349 | 3,900 | 1000 | | | 47 | | | | | |
| 3 | 302 | 10,000 | 1000 | 2.6 | 2.51 | 4 | 23.4 | 20.7 | 13.5 | 33.3 | 0.10 |
| 4 | 326 | 10,000 | 1000 | 2.6 | 2.51 | 9 | 19.5 | 24.2 | 16.5 | 29.7 | 0.20 |
| 5 | 333 | 10,000 | 1000 | 2.6 | 2.51 | 12 | 15.9 | 22.9 | 17.1 | 34.5 | 0.25 |
| 6 | 337 | 10,000 | 1000 | 2.5 | 2.06 | 16 | 10.3 | 19.0 | 14.0 | 47.5 | 0.25 |
| 7 | 342 | 10,000 | 1000 | 2.5 | 2.06 | 17 | 8.5 | 18.0 | 15.3 | 45.3 | 0.24 |
| 8 | 347 | 10,000 | 1000 | 2.5 | 2.90 | 18 | 9.3 | 21.1 | 18.6 | 36.8 | 0.29 |
| 9 | 334 | 5,600 | 1000 | 2.6 | 2.23 | 25 | 15.8 | 20.0 | 17.5 | 32.3 | 0.22 |
| 10 | 313 | 3,900 | 1400 | 2.6 | 1.90 | 19 | 36.5 | 23.7 | 11.6 | 19.7 | 0.23 |
| 11 | 337 | 3,900 | 1400 | 2.6 | 1.90 | 45 | 18.8 | 22.2 | 13.1 | 30.9 | 0.39 |
| 12 | 341 | 3,900 | 1400 | 2.6 | 1.90 | 54 | 12.8 | 16.7 | 16.0 | 34.9 | 0.45 |

TABLE XVIII

| Line | Temp. °C. | GHSV | Press. psig | $H_2/CO$ Molar Ratio | $CO_2$ in Feed Mole % | CO Conv. Mole % | Selectivity of CO to Mole % | | | | Production MeOH, g/g/hr |
|---|---|---|---|---|---|---|---|---|---|---|---|
| | | | | | | | MeOH | $Me_2O$ | $CH_4$ | $CO_2$ | |
| 13 | 314 | 3,700 | 500 | 2.9 | 2.81 | 12.0 | 17.6 | 57.2 | 3.4 | 21.0 | 0.19 |
| 14 | 317 | 3,700 | 500 | 3.2 | 2.00 | 13.0 | 14.9 | 48.6 | 3.4 | 32.4 | 0.16 |
| 15 | 327 | 3,700 | 500 | 3.1 | 2.35 | 15.0 | 13.9 | 53.0 | 4.8 | 27.2 | 0.21 |
| 16 | 297 | 3,600 | 1000 | 2.4 | 3.07 | 32.1 | 66.9 | 18.3 | 5.1 | 8.5 | 0.66 |
| 17 | 313 | 3,600 | 1000 | 3.3 | 2.25 | 34.3 | 40.5 | 25.9 | 7.9 | 19.3 | 0.45* |
| 18 | 320 | 3,600 | 1000 | 3.3 | 2.25 | 34.8 | 34.8 | 28.6 | 9.0 | 20.3 | 0.47 |
| 19 | 328 | 3,600 | 1000 | 3.3 | 2.25 | 34.3 | 32.7 | 30.7 | 10.2 | 24.4 | 0.43 |
| 20 | 293 | 3,600 | 1000 | 3.2 | 2.07 | 32.5 | 66.9 | 14.4 | 4.1 | 13.7 | 0.52 |
| 21 | 298 | 3,600 | 1000 | 3.2 | 2.07 | 32.3 | 65.1 | 16.8 | 4.8 | 12.3 | 0.52 |
| 22 | 253 | 3,600 | 1000 | 3.4 | 2.04 | 15.7 | 82.2 | 3.4 | 0.8 | 13.6 | 0.26 |
| 23 | 271 | 3,600 | 1000 | 3.4 | | 22.5 | 88.7 | 6.3 | 1.6 | 3.4 | 0.41 |
| 24 | 284 | 3,600 | 1000 | 3.4 | | 30.6 | 73.8 | 10.2 | 2.6 | 13.1 | 0.49 |
| 25 | 237 | 3,240 | 1400 | 3.0 | 2.94 | 12.0 | 100.0 | — | — | −0** | 0.22 |
| 26 | 271 | 3,240 | 1400 | 3.0 | 2.94 | 50.7 | 94.9 | 3.2 | 0.8 | 1.1 | 0.92 |
| 27 | 276 | 3,010 | 1400 | 2.8 | 2.61 | 48.2 | 92.1 | 3.0 | 0.8 | 4.1 | 0.84 |
| 28 | 291 | 3,010 | 1400 | 2.8 | 2.61 | 66.1 | 83.5 | 8.0 | 1.7 | 6.8 | 1.11 |
| 29 | 257 | 6,530 | 1400 | 2.7 | 2.88 | 12.6 | 92.3 | 2.2 | 0.6 | 4.9 | 0.47 |
| 30 | 306 | 6,530 | 1400 | 2.7 | 2.88 | 43.9 | 84.0 | 9.8 | 2.0 | 4.1 | 2.12 |
| 31 | 315 | 6,530 | 1400 | 2.7 | 2.88 | 49.2 | 71.0 | 14.5 | 3.0 | 11.4 | 1.70 |
| 32 | 325 | 6,530 | 1400 | 2.7 | 2.88 | 49.4 | 61.1 | 19.6 | 4.0 | 15.0 | 1.61 |
| 33 | 259 | 6,530 | 1000 | 3.1 | 2.45 | 14.6 | 87.6 | 2.9 | 0.6 | 8.9 | 0.49 |
| 34 | 276 | 6,530 | 1000 | 3.1 | 2.45 | 27.2 | 87.7 | 4.3 | 0.8 | 7.2 | 0.92 |
| 35 | 291 | 6,530 | 1000 | 3.1 | 2.73 | 36.3 | 83.7 | 7.3 | 1.5 | 7.5 | 1.22 |
| 36 | 269 | 9,180 | 1000 | 2.7 | 2.73 | 14.4 | 87.0 | 3.0 | 1.0 | 8.9 | 0.75 |
| 37 | 282 | 9,180 | 1400 | 2.7 | 2.73 | 20.7 | 87.3 | 4.5 | 1.1 | 7.1 | 1.10 |
| 38 | 295 | 9,180 | 1400 | 2.7 | 2.73 | 30.3 | 83.5 | 7.2 | 1.5 | 7.8 | 1.59 |
| 39 | 313 | 9,180 | 1400 | 2.7 | 2.73 | 38.3 | 74.4 | 12.8 | 2.5 | 10.4 | 1.93 |
| 40 | 263 | 3,200 | 1000 | 3.0 | 4.56 | 22.5 | 90.8 | 3.9 | 0.7 | 4.6 | 0.39 |
| 41 | 257 | 3,200 | 1000 | 3.0 | 4.56 | 17.4 | 91.4 | 2.9 | 1.0 | 4.8 | 0.30 |
| 42 | 254 | 3,270 | 1000 | 2.7 | 5.29 | 14.3 | 94.7 | 3.2 | 0.8 | 1.3 | 0.28 |
| 43 | 270 | 3,270 | 1000 | 2.7 | 5.29 | 26.4 | 93.2 | 4.4 | 1.0 | 11.3 | 0.52 |
| 44 | 268 | 3,410 | 1000 | 3.0 | 4.63 | 23.6 | 90.6 | 3.7 | 0.9 | 14.8 | 0.43 |
| 45 | 284 | 3,410 | 1000 | 3.0 | 4.63 | 39.0 | 84.5 | 7.4 | 1.4 | 6.7 | 0.69 |
| 46 | 288 | 3,410 | 1000 | 3.0 | 4.63 | 41.0 | 81.7 | 8.4 | 1.6 | 7.9 | 0.72 |
| 47 | 294 | 3,410 | 1000 | 3.0 | 4.63 | 42.7 | 76.4 | 11.0 | 2.1 | 10.3 | 0.72 |
| 48 | 298 | 3,410 | 1000 | 3.0 | 4.63 | 43.9 | 72.8 | 13.4 | 2.5 | 11.2 | 0.73 |
| 49 | 297 | 3,470 | 1000 | 3.3 | 2.60 | 44.7 | 72.4 | 15.2 | 2.8 | 9.5 | 0.73 |
| 50 | 291 | 3,470 | 1000 | 3.3 | 2.60 | 44.1 | 75.2 | 13.2 | 2.4 | 8.2 | 0.72 |
| 51 | 296 | 3,600 | 1000 | 2.9 | 4.55 | 43.5 | 73.9 | 13.7 | 2.6 | 9.5 | 0.80 |
| 52 | 292 | 3,600 | 1000 | 2.9 | 4.55 | 43.1 | 77.6 | 11.9 | 2.3 | 7.9 | 0.81 |
| 53 | 293 | 3,660 | 1400 | 3.1 | 4.66 | 59.6 | 84.5 | 8.9 | 2.2 | 4.1 | 1.14 |
| 54 | 296 | 3,660 | 1400 | 3.1 | 4.66 | 63.1 | 83.7 | 9.4 | 2.1 | 4.4 | 1.20 |
| 55 | 304 | 3,660 | 1400 | 3.1 | 4.66 | 66.1 | 81.1 | 14.0 | 3.4 | 1.2 | 1.29 |
| 56 | 290 | 6,800 | 1400 | 3.1 | 4.66 | 33.6 | 88.2 | 5.5 | 1.4 | 4.7 | 1.20 |
| 57 | 297 | 6,800 | 1400 | 3.1 | 4.66 | 39.9 | 77.1 | 6.0 | 14.2 | 2.5 | 1.27 |

TABLE XVIII-continued

| Line | Temp. °C. | GHSV | Press. psig | $H_2/CO$ Molar Ratio | $CO_2$ in Feed Mole % | CO Conv. Mole % | Selectivity of CO to Mole % | | | | Production MeOH, g/g/hr |
|---|---|---|---|---|---|---|---|---|---|---|---|
| | | | | | | | MeOH | $Me_2O$ | $CH_4$ | $CO_2$ | |
| 58 | 310 | 6,800 | 1400 | 3.1 | 4.66 | 47.8 | 78.3 | 11.2 | 2.3 | 7.8 | 1.64 |

*5.6% selectivity to i-butanol; 0.087 g/g/hr.
**$CO_2$ appeared to be consumed.

Lines 13 vs 17 illustrate that low pressure favors dimethylether formation while higher pressures favor methanol formation at higher rates. Lines 31 vs 39 show that as gas rates increase the production of methanol increases. Lines 40 through 49 and 3 through 8 demonstrate that higher yields of methanol are obtained at higher temperature.

The most significant entries are in lines 30, 31, 32, 38, 39 and 58. For each of these conditions the production of methanol is very high.

What is claimed is:

1. Crystalline copper aluminum borate having the significant x-ray diffraction lines set forth in Table A, a surface area of at least 5 square meters per gram and a pore volume of at least 0.04 cc per gram which is at least partially reducible with hydrogen under Temperature Programmed Reduction at a temperature no more than 350° C. to a composition comprising zero valent copper and $Al_4B_2O_9$.

2. The copper aluminum borate of claim 1 having the structure $Cu_{2-x}Al_{6-y}B_4O_{17}M_mM'_nM''_y$, wherein M is a divalent metal, M' is a monovalent metal, m ranges from 0 to 0.8, n ranges from 0 to 1.6, X ranges from 0 to 0.8 and is equal to the sum of m+n/2, M" is a trivalent metal and y ranges from 0 to 1.2.

3. The copper aluminum borate of claim 2 wherein m, n, y and X are 0.

4. Crystalline copper aluminum borate having the significant x-ray diffraction lines set forth in Table A, a surface area of at least 5 square meters per gram and a pore volume of at least 0.04 cc per gram, which is at least partially reducible with hydrogen under Temperature Programmed Reduction at a temperature no more than 350° C. to a composition comprising zero valent copper and $Al_4B_2O_9$ wherein said copper aluminum borate has the structure $Cu_{2-x}AlB_4O_{17}M_x$ wherein m is a divalent metal selected from the group consisting of zinc, cobalt, nickel and magnesium and X is a number ranging from 0.01 to 0.8.

5. The copper aluminum borate of claim 4 wherein X is a number from 0.05 to 0.50.

6. The copper aluminum borate of claim 5 wherein M is zinc.

7. The copper aluminum borate of claim 5 wherein M is cobalt.

8. The copper aluminum borate of claim 5 wherein M is nickel.

9. The copper aluminum borate of claim 5 wherein M is magnesium.

10. A composition comprising crystalline copper aluminum borate of claim 1 and $Al_4B_2O_9$.

11. A composition comprising crystalline copper aluminum borate of claim 1 and copper chromite.

12. The process of preparing copper aluminum borate which comprises (1) combining a source of divalent copper, trivalent aluminum and boron in the form of the oxide or borate, (2) drying the composition and (3) calcining the composition at a temperature sufficiently high to form a crystalline copper aluminum borate having the significant x-ray diffraction lines set forth in Table A wherein the composition of step (1) comprises at least one volatile component.

13. The process of claim 12 wherein step 1 is carried out in an aqueous medium.

14. The process of claim 13 wherein step 1 is carried out in the presence of aqueous ammonia or aqueous ammonium salt.

15. The process of producing copper aluminum borate which comprises (1) combining a source of divalent copper, trivalent aluminum and boron in the form of the oxide or borate in an aqueous medium, (2) drying the composition to remove water and (3) calcining the composition at a temperature sufficiently high to form crystalline copper aluminum borate having the significant x-ray diffraction lines set forth in Table A.

16. The process of claim 15 wherein step 1 is carried out in the presence of aqueous ammonia or aqueous ammonia salt.

17. The process of claim 16 wherein calcination is carried out at a temperature of at least 700° C.

18. The process of claim 16, wherein calcination is carried out at a temperature of at least 800° C.

19. A composition comprising finely divided zero valent copper on a support comprising at least one member selected from the group consisting of $Al_4B_2O_9$ and copper aluminum borate formed by the reduction of the crystalline copper aluminum borate of claim 1.

20. The process of producing a composition comprising finely divided zero valent copper on a support comprising at least one member from the group consisting of $Al_4B_2O_9$ and crystalline copper aluminum borate which comprises contacting the crystalline copper aluminum borate of claim 1 with a reducing agent.

21. The process of claim 20 wherein the copper aluminum borate is contacted with a reducing agent at a temperature of at least 175° C.

22. The process of claim 20 wherein the reducing agent comprises carbon monoxide.

23. The process of claim 20 wherein the reducing agent comprises hydrogen.

* * * * *

UNITED STATES PATENT OFFICE
CERTIFICATE OF CORRECTION

Patent No. 4,729,979  Dated March 8, 1988

Inventor(s) Alex Zletz

It is certified that error appears in the above-identified patent and that said Letters Patent are hereby corrected as shown below:

Patent reads:

| Col. | Line/s | |
|---|---|---|
| 3 | 32 | "gas" and should read --was-- |
| 4 | 10 | "...+$2H_2 43Al_2O_3$..." and should read --...+$2H_2 \rightarrow 3Al_2O_3$...-- |
| 5 | 36 | "710.042" and should read --710,042-- |
| 29 | 47 | "wherein m is" and should read --wherein M is-- |

Signed and Sealed this

Fifth Day of July, 1988

Attest:

DONALD J. QUIGG

Attesting Officer

Commissioner of Patents and Trademarks